United States Patent [19]

Rüsch et al.

[11] 3,962,519
[45] June 8, 1976

[54] RUBBER ARTICLE OR INSTRUMENT AND METHOD OF PRODUCING THE SAME

[75] Inventors: Werner Rüsch, Rommelshausen; Heinrich Beer, Geradstetten; Veronika Seeger, Stuttgart-Bad Cannstatt; Manfred Waibel, Schornbach, all of Germany

[73] Assignee: Messrs. Willy Rusch, K.G., Germany

[22] Filed: Apr. 22, 1974

[21] Appl. No.: 463,170

Related U.S. Application Data

[63] Continuation of Ser. No. 373,760, June 26, 1973, abandoned, which is a continuation of Ser. No. 158,067, June 29, 1971, abandoned, which is a continuation-in-part of Ser. No. 818,247, April 22, 1969, abandoned.

[30] Foreign Application Priority Data

Apr. 26, 1968  Germany............................ 1766265

[52] U.S. Cl............................ 428/409; 128/DIG. 21; 260/3; 260/375 B; 260/824 R; 428/447; 428/451

[51] Int. Cl.²................... A61M 25/00; A61B 1/00; A61B 17/00; B32B 25/20

[58] Field of Search................. 260/37 SB, 29.1 SB, 260/161, 824 R, 3; 161/164, 206, 208; 128/DIG. 9, DIG. 16, DIG. 21; 428/409, 447, 448, 451

[56] References Cited
UNITED STATES PATENTS

| | | | |
|---|---|---|---|
| 2,470,772 | 5/1949 | Haas................................. | 117/139 |
| 3,021,292 | 2/1962 | Hurd et al............................. | 260/3 |
| 3,034,509 | 5/1962 | Bernstein........................... | 128/348 |
| 3,730,938 | 5/1973 | Smith et al..................... | 260/37 SB |
| 3,762,978 | 10/1973 | Holmes et al.................. | 161/206 X |
| 3,794,556 | 2/1974 | Young............................. | 161/206 |

OTHER PUBLICATIONS

Noll; Chemistry & Technology of Silicones, Academic Press, 1968, pp. 457–459, 471.

*Primary Examiner*—Harold Ansher
*Attorney, Agent, or Firm*—Craig & Antonelli

[57] ABSTRACT

Rubber articles, such as medical, surgical or hygienic instruments, are produced from a rubber material in which are incorporated high molecular weight silicon compounds which are at least partly capable of migrating in the rubber material so that a water repellent and adherence inhibiting effect of the surface of the articles can be maintained.

10 Claims, 1 Drawing Figure

U.S. Patent  June 8, 1976  3,962,519
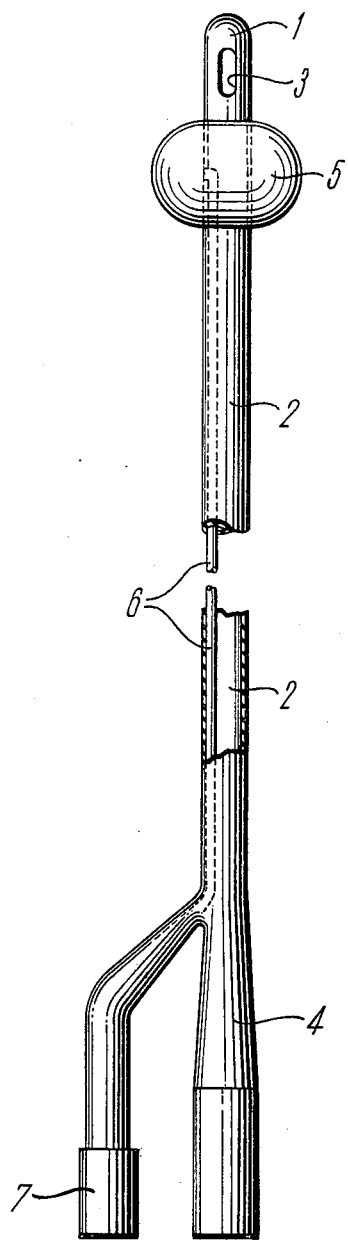
INVENTORS
WERNER RUSCH, HEINRICH BEER,
BY    VERONIKA SEEGER and
      MANFRED WAIBEL
Craig, Antonelli, Stewart & Hill ATTORNEYS

RUBBER ARTICLE OR INSTRUMENT AND METHOD OF PRODUCING THE SAME

The present application is a continuation application of application Ser. No. 373,760, filed June 26, 1973 and now abandoned, which in turn is a continuation application of application Ser. No. 158,067, filed June 29, 1971 and now abandoned which in turn is a continuation-in-part application of application Ser. No. 818,247, filed Apr. 22, 1969 and now abandoned.

This invention relates to rubber articles, in particular to rubber instruments intended to be used for medical, surgical or hygienic purposes.

Medical, surgical and hygienic instruments made from rubber, such as catheters, probes, rubber tubes, have certain disadvantages which arise from the loose structure of the rubber and which become particularly apparent with increasing use involving repeated cleaning and sterilization operations. Absorption of moisture also increases with use in these instruments. Thus latex catheters which remain in the body of a patient for a prolonged period of time and thereby come into contact with urine, swell in the latter. Also the ability of the rubber to slide is inherently low and decreases further after some time. Simultaneously the rubber loses progressively its tendency to repel adhesive matter, so that blood, pus, serum and so on remain adhering to the instruments in an undesirable manner.

These disadvantages can be avoided temporarily by applying a silicone oil or grease to the surface. However, the silicone layer deposited on the surface may be washed away during a single use of the instrument, or at the latest when the instrument is cleaned, so that the silicone oil or grease must be reapplied prior to each use of the instrument. However, the silicone oil is also washed away during sterilization with dry steam which precedes its use, by the steam and condensing steam, or by hot water. If the silicone oil or grease is applied after sterilization, it is imperative that sterile silicone be used. Sterile silicone is not usually used and its use involves too much difficulty.

Furthermore, attempts have been made to produce medical instruments from silicone rubber. However, in many cases the strength of silicone rubber is too low, and it is disproportionately expensive.

When cotton fibers are treated with latex by a dipping method, low molecular weight silicone oils in the form of an emulsion are conventionally added to the latex mixture in order to avoid the formation of froth as well as of a skin on the surface of the latex. These silicone oils weep out of the latex mixture during the treatment. Finally, it is also known to emulsify high molecular weight silicones and to spray them as release agents into molds in order that for example an extruded or cast article can be released more easily from the mold.

These disadvantages of the known rubber instruments are avoided by the invention, and instruments are provided with a surface which is hydrophobic or repels water and material which might adhere thereto; these properties make the instruments easily slidable and protects them against attack by water. It is important in this case that these surface properties of the instruments be maintained for a long period of time.

The medical, surgical and hygienic rubber instruments according to the invention, contain in the rubber, at least in the layers disposed under the surface, high molecular weight organic silicone compounds which however can at least in part still migrate in the rubber. In contrast to the known instruments the rubber instruments according to the invention thus provide not merely a superficial layer of silicone compounds, but contain considerably larger quantities of silicone compounds which are embedded in the rubber material itself. A further essential difference between the rubber instruments according to the invention and the known instruments coated with low molecular weight silicone oils or greases, resides in the fact that in the instruments according to the invention the silicon compounds are of high molecular weight, that is to say in general they have a semi-liquid oily to semi-solid wax-like consistency. Because of this physical state of the silicon compounds the migration speed of the silicon compounds in the rubber is so low that they migrate out of the latter only very slowly.

On the other hand, the migration speed of the silicon compounds in the rubber material is still sufficiently high that a sufficient quantity of silicon compounds is always present at the surface of the instrument to maintain desired properties on the instrument surface. The surface film of high molecular weight silicon compounds is not as easily washed away from the instruments as the known surface film of low molecular weight silicone oils or greases. If, however, the surface film is in fact washed away, it is always replenished again by migration of the silicon compounds, from the inner part of the bulk of the instruments. This replenishment being possible for many years.

In this way the instruments are also durably protected against undesirable water absorption. Furthermore this continuous surface film of high molecular weight silicon compounds provides good protection against ageing due to the effects of light and heat. The instruments according to the invention demonstrate in a particular manner the water repellent and inactivating effects of the silicone layer. For example, a deposition of crystals from cooling urine in catheters and adhesion thereof at the inner wall of the catheter is prevented. When applying tampons to open operating wounds in body cavities, thin walled rubber balloons are used which are attached to the instrument and which are blown up by air or a sterile liquid after insertion into the said body cavity. The compression effected thereby causes the flow of blood to stop. When the surface of the balloon is not siliconized, the balloon adheres to the wound and opens it up again when the instrument is removed. With siliconized instruments, perfect release and separation are effected. This effect is particularly important in the use of a Sengstaken probe which serves for stopping the blood flow by compression in the case of oesophagus varices.

Natural rubber, mixtures of natural rubber and synthetic rubber, or synthetic rubber alone may be used as rubber material for the instruments. The fact that the high molecular weight silicon compounds are embedded in the rubber material thus makes it unnecessary to use silicone rubber as basic material for these instruments.

The high molecular weight silicon compounds have in general a viscosity of more than 60,000 centistokes (cSt). The molecular weight of the high molecular weight silicon compounds lies in general above 90,000. Particularly suitable silicon compounds are high molecular weight polysiloxanes which under certain circumstances may be cross-linked for example, polydimethyl siloxane, consequently also called dimethylpolysiloxane, having a molecular weight of more than 100,000. Organic silicon compounds employable in the present invention are defined by the formula:

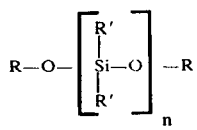

wherein R represents hydrogen, methyl, ethyl, propyl, butyl or $Si(CH_3)_3$, R' represents hydrogen, methyl, ethyl or phenyl, and n represents any number which yields the desired molecular weight of the compounds.

The ability of the high molecular weight silicon compounds to migrate in the rubber material depends substantially upon their molecular weight, but also their structure, such as side chains and cross-links, has an effect thereon. In general the silicon compounds should range from liquid to wax-like.

The proportion of the high molecular weight silicon compounds in the rubber instruments may vary within wide limits. Good results are obtained with proportions of approximately 0.1 to 10% by weight of high molecular weight silicon compounds related to the rubber quantity in the instrument. In general however, a quantity of the silicon compound amounting to about 5% by weight should be perfectly sufficient. In particular in instruments with thick-walled material, it is even sufficient that the silicon compounds are embedded only in the regions of the rubber material lying below the surface.

The production of the instruments according to the invention, in particular the process of embedding the silicon compounds, may be effected in various ways. A normally preferred method for producing medical instruments from natural rubber is described below by way of example, and reference thereto will facilitate the understanding of the various ways available to effect embedding of the silicon compounds.

The production starts in general from plantation latex when the formed article is to be produced by a dipping method or by casting. In this case, the vulcanization additives, which under certain circumstances may be in the form of aqueous dispersions, are worked into the latex whereby a mineralized latex milk is obtained. The latex milk is formed by dipping a matrix into the latex milk or by casting the latex milk, and the latter is coagulated at the same time or subsequently thereto by the effect of heat or the addition thereto of an acid. The coagulated article of latex rubber obtained thereby is then de-watered and thereafter subjected to a vulcanization process. For example, latex catheters are produced according to this method.

In one embodiment of the method according to the invention for producing medical, surgical or hygienic instruments, silicon-containing compounds are used which are already in a high molecular weight form before they are embedded in the rubber material. The high molecular weight silicon compounds are added to the rubber material prior to the formation thereof, and may be in the form of an emulsion or in a pure form. If the production of medical, surgical or hygienic instruments starts from plastic rubber mixtures, e.g. plantation rubber, the high molecular weight compounds may be mixed into this plantation rubber before or after the vulcanization additives have been added thereto, and may be in the form of an emulsion or in the form of an oil. However it is also possible to add emulsions of the silicon containing compounds to the latex itself during the production of the plastic rubber material from a latex, so that a plastic rubber material is used as starting material which contains the high molecular weight silicon compounds. If the instruments are produced from latex milk by the dipping method, the silicon-containing high molecular compounds are preferably added to the latex milk in the form of emulsions. This mixing-in of the silicon-containing compounds may be effected in this case also before, during, or after the addition of the vulcanization additives.

In another embodiment of the method for producing the medical, surgical or hygienic instrument according to the invention, first the low molecular weight silicon-containing compounds which are suitable for treatment to high molecular weight substances are introduced into the rubber material, and these low molecular weight silicon compounds are then converted in the material into the high molecular weight form. The low molecular weight silicon compounds used may contain one or more silicon atoms and are preferably compounds which can be converted into high molecular weight silicon compounds by condensation, addition or polymerization under certain circumstances with the formation of co-polymers. The low molecular weight organic silicon compounds referred to herein are understood to be, in particular, compounds the viscosity of which is so low that they would weep too quickly out of the rubber material. In general the molecular weight of these low molecular weight organic silicon compounds lies below approximately 90,000. Low molecular weight compounds which can be converted into high molecular weight organic silicon compounds, have reactive groups which can react with reactive groups of other molecules. The low molecular weight compounds should be convertible into the high molecular weight compounds embraced by the aforementioned formula.

The low molecular weight organic silicon compounds can be mixed with the rubber material prior to the formation thereof and may be in the form of emulsions or in unmixed form or undissolved form, as commonly used in trade. Thus, emulsions of the low molecular weight organic silicon compounds can be mixed with a rubber latex which is then coagulated and converted into a mineralized plastic rubber mixture. The choice of the individual low molecular weight silicon compounds depends upon the fact that during the further treatment of the rubber mixture, in particular during vulcanization, the originally present low molecular weight silicon compounds must with certainty be converted into high molecular compounds.

In this case, for example condensations, additions to double bonds, or also polymerization or olefin groups, in particular allyl groups, may take place. When a latex is treated to produce the formed articles, the low molecular weight silicon compound is mixed with this latex, preferably in the form of an emulsion. When a latex is treated by a dipping method, the low molecular weight silicon compound should be converted into a high molecular weight compound preferably prior to the dipping because otherwise it might happen in the case of repeated dipping that the low molecular weight compound sweats out of the deposited rubber mixture after the first or second dip to such extent that the following layers to be deposited cannot adhere sufficiently to the already deposited layers because of the strong release effect of the organic silicon compound.

The invention will be more easily understood by reference to the following examples.

EXAMPLE 1.

167 g natural rubber latex are stabilized in a glass beaker with 0.5 g of a 20% solution of Emulvin W, the latter being introduced with gentle stirring. After 5 minutes 2 g ageing protecting means such as DDA-Emulsion is added thereto. After a further 5 minutes a paste of 1 g colloidal sulphur, 2 g active zinc oxide, 1 g Vulkacit LDA and 4 g water is added thereto. Directly afterwards a paste of 1 g Aerosil and 9 g water is added. After ten minutes stirring 1 g silicone emulsion is added thereto. This emulsion consists substantially of equal quantities by weight of silicone oil or grease, and water. Furthermore, it contains a small quantity of non-ionizing emulsifier. The silicone oil is a polydimethylsiloxane having a viscosity of approximately 70,000 cSt, corresponding to a mean molecular weight of approximately 100,000. This organic silicon compound contains terminal methyl groups and a small proportion of terminal OH-groups so that under certain circumstances an enlargement of the molecule is still possible.

The latex mixture is used for producing latex balloon catheters by the dipping method. Dipping rods of stainless steel are dip-coated with several layers of the latex mixture, a certain drying time being maintained after each coating process. After the prescribed wall thickness has been obtained, the catheters are removed, dried and washed in order to remove the water-soluble fractions of the latex, the additives and the silicone emulsion, are dried once more and finally vulcanized for 10 minutes at 100°C in dry steam.

After vulcanizing, the catheters have a smooth and bland, but not smeary surface. Water forms globules on the surface without wetting. Attempts to stick labels and the like on the adhesive repellent surface with conventional rubber adhesives fail. Marking by means of generally used marking ink is possible only after the respective area has been wiped with a rag soaked in petroleum spirit (gasoline). 2 to 3 hours after wiping, the marking ink adheres badly again which is a proof of the fact that in the intervening period sufficient silicone has wept out to make the surface repellent.

EXAMPLE 2.

The following latex mixture is produced:

| | |
|---|---|
| Natural rubber latex | 167 g |
| Emulvin W, 20% | 1 g |
| DDA Emulsion | 3 g |
| Pliolite-Latex 151 | 10 g |
| Colloidal Sulphur | 1 g |
| Vulkacit LDA | 0.5 g |
| Active zinc oxide | 1.0 g |

The last three ingredients made into a paste with 2.5 gm water.

After mixing all the items together, 6 g of 50% silicone emulsion which contains further a small quantity of a non-ionizing emulsifier is added to the mixture. The silicone oil is a polydimethylsiloxane having a viscosity of approximately 70,000 cSt corresponding to a mean molecular weight of approximately 100,000. It has terminal methyl groups and a small proportion of terminal OH—groups, so that an expansion of the molecule is still possible under certain circumstances.

This latex mixture is poured in a layer of 3 mm thickness into a Petri dish and permitted to dry. The dried rubber disc is washed in water for 24 hours, dried again at 70°C and vulcanized at 120°C and 4 atmospheres pressure in hot air for 30 minutes.

The vulcanized rubber plate has a smooth and bland surface, water forms globules thereon without wetting; the rubber surface is strongly adhesive repellent. The water adsorption for a plate 1.5 mm thick amounts to approximately 3% in 24 hours at 40°C.

EXAMPLE 3.

The following natural rubber latex mixture is produced:

83.5 g natural latex 60% and 83.5 g Revultex MR are mixed together and stabilized with 2 g of a 20% solution of Emulvin. 3 g ageing protection means DDA-Emulsion and 3 g of a 15% solution of Lutonal M40 are added thereto. 1 g colloidal sulphur, 0.25 g active zinc oxide and 0.25 g Vulkacit LDA are mixed with water to form a paste and are added thereto.

After mixing together, a 30% solution of formaldehyde is added thereto drop by drop with continuous stirring until the pH value of the mixture has dropped to 9.1. Thereafter 4 g silicone emulsion are added thereto. This latex mixture is heat sensitive. A test tube is filled with water having a temperature of 60°C and the tube is inserted about half way into the latex mixture. In the course of from 1 to 2 minutes a coagulated layer of approximately 3 mm thickness is deposited thereon. After this coagulated layer has been dried, a rubber bag is obtained which is transparent and has typical silicone properties after washing in water, drying and vulcanizing it is water repellent, has reduced water absorption, and has an adhesive repellent effect. The surface becomes smooth and bland after a few days storage.

EXAMPLE 4.

The following latex mixture is prepared:

200 g Neoprene latex 571, 50% are mixed with 20 g Styrene-butadiene latex 85/15, 50% 3 g Aquarex SMO, 33%, are added thereto and the mixture is stirred for 5 minutes. Then 3 g DDA-Emulsion is added thereto and after a further 5 minutes a paste prepared from 5 g active zinc oxide, 1 g sulphur, 1 g mercaptoimidazolin and 7 g water is added thereto.

After mixing together 4 g silicone emulsion, and after stirring for 5 minutes 0.08 ccm of a 40% emulsion of methyl-hydrogen-polysiloxane and 0.02 and ccm of a 10% emulsion of di-butyl-stannic laurate are added thereto.

The silicone emulsion contains from 30 to 70% of a polydimethylsiloxane with terminal OH-groups and a viscosity of approximately 80,000 cSt corresponding to a mean molecular weight of approximately 128,000.

The methyl-hydrogen-polysiloxane emulsion contains up to 40% of an organic silicon compound which can be obtained by hydrolysis of $CH_3 H Si Cl_2$ in water. This refers to a silicone oil the chain length of which is kept short by terminal trimethylsilyl groups and which in the presence of dibutlystanniclaurate reacts with the OH-groups of the emulsion giving off hydrogen and having a cross-linking effect. The consequence therefore is an enlargement of the molecule and an increase of the viscosity of the polydimethylsiloxane initially added thereto.

The surgical rubber instruments obtained from this latex mixture and produced in accordance with known dipping methods are washed in water, dried and vulcanized (20 minutes at 140°C in hot air at a pressure of two atmospheres) and have thereafter a water repellent and adhesive repellent surface. Since this rubber substance is more swelling resistant against solvents than natural rubber an interesting experiment can be made therewith: the article is placed for approximately 1 hour into pure previously distilled hexane. Swelling is insignificant. After the hexane has been distilled off a residue remains which originates from the rubber substance, but which contains less than 1% silicon compounds. If the experiment is made with an article produced from a similar mixture but without the addition of methyl-hydrogen-polysiloxane a residue with a silicon content of more than 10% is obtained. It may be seen therefrom that the cross-linking of the dimethylpolysiloxane must have led to decreased solubility.

One embodiment of the invention is described below by way of example with reference to the accompanying drawing which is a plan view illustrating a balloon catheter of latex.

The catheter has been produced by the method according to Example 1, and has a solid leading end portion 1 followed by a long tubular catheter body 2 provided with an opening 3 which leads into the interior of the tubular body. The trailing or rear end 4 of the tubular body 2 is enlarged in a funnel-like manner. A balloon 5 illustrated in the filled or blown up state is located immediately behind the solid end portion. An air duct 6 extends through the tubular body, one end of the duct terminating in the balloon, the other end being laterally guided out of the tubular catheter body and closed by a valve 7. In the empty state the balloon is flush with the catheter body.

The invention being thus described, it will be obvious that the same may be varied in many ways. Such variations are not to be regarded as a departure from the spirit and scope of the invention, and all such modifications as would be apparent to one skilled in the art are intended to be included herein.

We claim:

1. A rubber article for use as a medical or sanitary instrument which comprises individual layers of a rubber material firmly adhering to one another, said rubber material containing, based on the amount of rubber, about 0.1 to 10% by weight of organic silicon compounds having the general formula

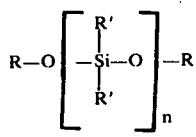

wherein R represents hydrogen, methyl, ethyl, propyl, butyl or Si(CH$_3$)$_3$, and R' represents hydrogen, methyl, ethyl or phenyl, and $n$ represents a number which yields a molecular weight for said silicon compounds of more than 90,000, the organic silicon compounds exhibit a viscosity of at least 60,000 centistokes and are incorporated into the rubber without a chemical bond so that they are at least partially migratory within said rubber material.

2. An article as claimed in claim 1, wherein the rubber material contains approximately 5% by weight of the silicon compound.

3. An article as claimed in claim 1, wherein the high molecular silicon compounds are polysiloxanes which may be cross-linked.

4. An article as claimed in claim 1, wherein the rubber within said rubber material is natural rubber, synthetic rubber, or a mixture of natural and synthetic rubber.

5. An article as claimed in claim 1, wherein said silicon compunds are cross-linked polysiloxanes.

6. An article as claimed in claim 1, wherein said silicon compounds are polydimethyl siloxanes.

7. A medical or sanitary rubber instrument consisting of individual layers of a rubber material firmly adhering to one another, the rubber material at least in the layers disposed under the surface of said instrument containing, based on the amount of rubber within said rubber material, about 0.1 to 10% by weight of an organic silicon compound which can at least in part migrate within the rubber of said rubber material whereby a sufficient quantity of the silicon compound is present at the surface of the instrument to maintain a surface which is hydrophobic and repels water and material which might adhere thereto, said organic silicon compound having the general formula.

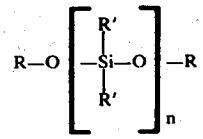

wherein R represents hydrogen, methyl, ethyl, propyl, butyl or Si(CH$_3$)$_3$, and R' represents hydrogen, methyl, ethyl or phenyl, and $n$ represents a number which yields a molecular weight for said silicon compounds of more than 90,000; said organic silicon compound exhibiting a viscosity of at least 60,000 centistokes.

8. The instrument as claimed in claim 7, wherein the rubber material contains approximately 5% by weight of the silicon compound.

9. The instrument as claimed in claim 7, wherein the high molecular weight silicon compound is a polysiloxane which may be cross-linked.

10. The instrument as claimed in claim 7, wherein the rubber within said rubber material is natural rubber, synthetic rubber, or a mixture of natural and synthetic rubber.

* * * * *